United States Patent
Gull et al.

[11] Patent Number: 6,057,334
[45] Date of Patent: May 2, 2000

[54] BENZO[G]QUINOLINE DERIVATIVES

[75] Inventors: Peter Gull, Pfeffingen, Switzerland; Rudolf Markstein, Rheinfelden, Germany; Max Peter Seiler, Riehen, Switzerland

[73] Assignee: Novartis AG, Basel, Switzerland

[21] Appl. No.: 09/214,537

[22] PCT Filed: Jul. 7, 1997

[86] PCT No.: PCT/EP97/03582

§ 371 Date: Jan. 6, 1999

§ 102(e) Date: Jan. 6, 1999

[87] PCT Pub. No.: WO98/01444

PCT Pub. Date: Jan. 15, 1998

[30]     Foreign Application Priority Data

Jul. 8, 1996 [GB] United Kingdom ............... 9614282
Dec. 16, 1996 [GB] United Kingdom ............... 9626093

[51] Int. Cl.$^7$ ........................ A61K 31/473; C07D 401/12
[52] U.S. Cl. ............................. 514/290; 546/101
[58] Field of Search ................ 546/101; 514/290

[56]          References Cited

U.S. PATENT DOCUMENTS 4,565,818  1/1986  Nordmann et al. ............ 546/101
5,262,422  11/1993  Gull et al. .................... 546/101

FOREIGN PATENT DOCUMENTS 077 754    4/1983  European Pat. Off. .
373 658 A2 6/1990  European Pat. Off. .
512 952   11/1992  European Pat. Off. .
659 430    6/1995  European Pat. Off. .
2729145-A1 7/1996  France .
WO 90/00896 2/1990 WIPO .

OTHER PUBLICATIONS

P. Luvone et al., Investigative Ophthamology & Visual Science, vol. 32, No. 5, pp. 1674–1677 (1991). *
Chemical Abstracts 127:76436.
Chemical Abstracts 126:198252.
Chemical Abstracts 125:265927.
Chemical Abstracts 125:48966.
Derwent Abstract 96–343937.

*Primary Examiner*—Mukund J. Shah
*Assistant Examiner*—V. Balasubramanian
*Attorney, Agent, or Firm*—R. Scott Meece; Robert J. Gorman, Jr.

[57]           ABSTRACT

The invention provides a compound of formula (I) wherein A, B, X, Y and R are as defined in the description, and a process for preparing them. The compounds of formula (I) arc useful as pharmaceuticals for the treatment of glaucoma and myopia.

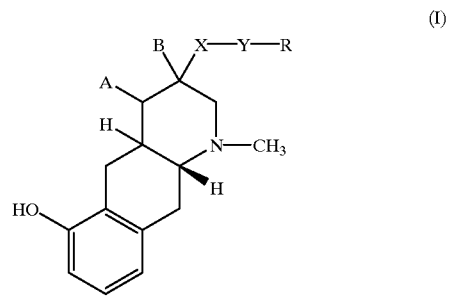

12 Claims, No Drawings

BENZO[G]QUINOLINE DERIVATIVES

The present invention relates to novel benzo[g]quinoline derivatives, their preparation, their use as pharmaceuticals and pharmaceutical compositions containing them.

More particularly the present invention provides a compound of formula I

I wherein

A and B are each H or form together an additional bond,

X is $CH_2$ or CO,

Y is O, S, S=O, $NR_1$ [$R_1$ being H or $(C_{1-4})$alkyl], $CH_2$ or O—$CH_2$, and R is of formula (a), (b), (c), (d), (e), (f), (g), (h) or (i)

(a)

(b)

(c)

(d)

(e)

(f)

(g)

(h)

(i)

wherein $R_1$ is defined above, $R_2$ is H or trifluoromethyl, $Z_1$ is O, S or NH and $Z_2$ is CH or N, provided that if X is $CH_2$, Y is S and R is of formula (a) wherein the free bond is adjacent to the nitrogen and $R_2$ is H, then A and B are not H, in free base or acid addition salt form.

The above-defined alkyl groups preferably represent methyl.

X preferably is $CH_2$.

Y preferably is O or S.

The compounds of the invention possess asymmetrical centers in positions 3, 4a and 10a, and possibly in the X—Y—R substituent. They may therefore appear in optically active form or in form of mixtures of optical isomers, e.g. in form of racemic mixtures. All optical isomers and their mixtures including the racemic mixture are part of the present invention.

In a group of compounds of formula I, A and B are each hydrogen, X is $CH_2$, Y is O or S and R is of formula (b) or (c).

In a further group of compounds of formula I, A and B form together an additional bond, X is $CH_2$, Y is O or S and R is of formula (a) or (e).

In still a further group, A and B and X are as defined above, Y is O, S, $NR_1$ [$R_1$ being H or $(C_{1-4})$alkyl], $CH_2$, or O—$CH_2$, and R is of formula (a), (b), (c), (d), or (g), wherein $R_1$ is as defined above and $R_2$ is H, or of formula (e) or (f), wherein $R_1$ is H, $Z_1$, is O or S and $Z_2$ is CH.

When A and B are each H, the X—Y—R substituent preferably presents the configuration 3R.

In a further aspect the invention provides a process for the production of the compounds of formula I and their acid addition salts, whereby in a compound of formula II

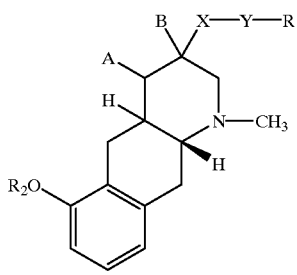

II

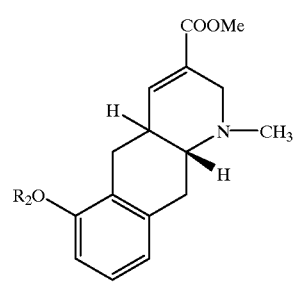

III$_b$ wherein A, B, X, Y and R are as defined above and $R_2$ is $(C_{1-4})$alkyl, the alkoxy group is converted into a hydroxy group, and the compounds of formula I thus obtained are recovered in free base or acid addition salt form.

The reaction can be effected according to known methods, e.g. using hydrobromide acid or boron tribromide. In formula II, $R_2$ is preferably methyl.

Working up the reaction mixtures obtained according to the above process and purification of the compounds thus obtained may be carried out in accordance to known procedures.

Acid addition salts may be produced from the free bases in known manner, and vice versa. Suitable acid addition salts for use in accordance with the present invention include for example the hydrochloride.

The starting compounds of formula II wherein A and B are each H may be produced from the corresponding compounds of formula III$_a$

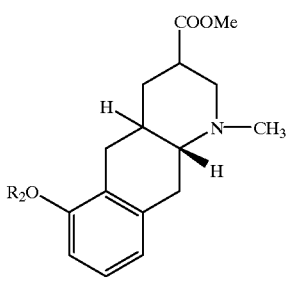

III$_a$ wherein $R_2$ is as defined above, for example as described in Example 1.

The compounds of formula III$_a$ are known or may be produced in analogous manner to known procedures.

The starting compounds of formula II wherein A and B together form an additional bond may be produced from the corresponding compounds of formula III$_b$ wherein $R_2$ is as defined above, for example as described in Example 24.

The compounds of formula III$_b$ may be produced from compounds of formula X according to the following reaction scheme:

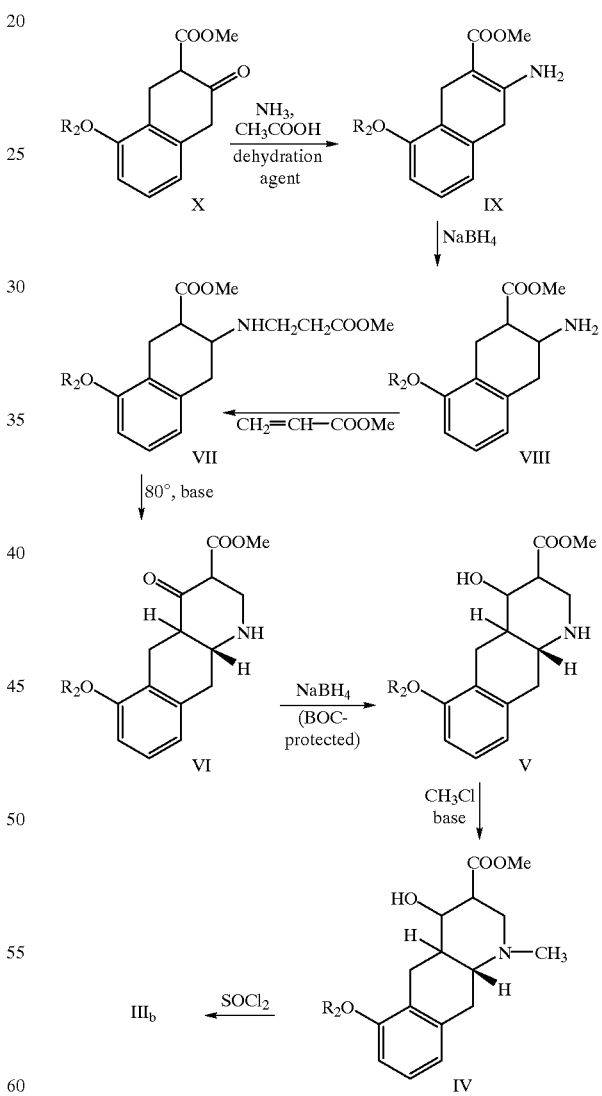

All the reactions in this scheme may be carried out according to known procedures.

The compounds of formula X are k n own or may be produced in analogous manner to known procedures.

The compounds of formula I and their physiologically acceptable acid addition salts, referred to hereinafter as agents of the invention, exhibit valuable pharmacological properties in animal tests and are therefore useful as pharmaceuticals.

In particular, the agents according to the invention effect a decrease on the intraocular pressure in rabbits, at doses of 0.1 to 100 μmol. Male rabbits of ca. 3 to 6 kg are fixed in cages leaving their heads free. The solutions with the compound to be tested are applied to the right eye and the placebo solutions to the left eye (50 μl each). The eyes are firstly anesthetized with a drop of a solution containing 0.4% Novesine (Ciba Vision Ophthalmics, Switzerland) and the ocular pressure is determined at various intervals after administration (10, 30, 60, 120, 180 and 240 minutes), whereby a pneumatonometer (Mentor 0 & 0 Inc., Norwell, USA) is used.

The agents according to the invention are therefore useful in the treatment of glaucoma.

Moreover the agents of the invention increase the blood flow in the optic nerve, as indicated by experiments performed as described by M. Rudin and A. Sauter in Non-invasive determination of regional cerebral blood flow in rats using dynamic imaging with Gd(DTPA), Magnetic Res. in Med. 22, 32–46 (1991). In this test, rats are anesthetized with isoflurane. The femoral vein is cannulated for injection of the paramagnetic contrast agent Gd(diethylentriaminepenta-acetate). Determination of blood flow (ml/100g/min.) by NMR imaging is performed immediately before and 30 min. after s.c. drug administration. Experiments are performed double blind in groups of 8–26 animals. In a first series of experiments, the whole optic nerve is measured. In a second series, the effect on subregions of the optic nerve including the proximal part with the head of the optic nerve is determined.

In this test, the agents of the invention at doses of 0.1 to 0.5 mg/kg s.c. significantly improve blood flow to the optic nerve but not in the striatum. In the second series of experiments, the agents of the invention at the indicated doses preferentially enhance blood perfusion in the proximal part of the optic nerve including the head and in the distal part.

The agents of the invention are therefore useful in conditions where prevention or delay of progressive atrophy of the optic nerve is desirable, for example in conditions where the visual fields are impaired and particularly in glaucoma forms which are not characterized by an increase of the intra-ocular pressure (low tension glaucoma), in which standard glaucoma therapy including β-blockers is ineffective.

The agents of the invention furthermore exhibit dopaminominetic activity, as evidenced in vitro, e.g. by their ability to inhibit electrically evoked acetylcholine release from striatal slices [R. Markstein et al., J. Neural. Transm. 103, 17–30 (1996] at concentrations of 1 to 100 nM.

Eye permeable dopaminamimetic compounds have been indicated to prevent development of myopia in man [P. M. Iuvone et al., Inv. Ophthal Vis. Sci. 32,1674–1677 (1991)].

The agents of the invention are therefore useful in the treatment of myopia, as can be confirmed in standard tests, e.g. in the model according to R. A. Stone et al. [Proc. Natl. Acad, Sci. (USA) 86, 704–706 (1989)] wherein experimental myopia is produced in chickens, on administration of about 0.1 to about 1 mg/kg in eye drops.

For the above mentioned indications, the appropriate dosage will of course vary depending upon, for example, the compound employed, the host, the mode of administration and the severity of the condition being treated. However, in general, satisfactory results in animals are indicated to be obtained at a daily dosage of from about 0.1 to about 100 μmol in ophthalmological solution. In larger mammals, for example humans, indicated daily dosages are in the same range, preferably in the range from about 0.1 to about 10 μmol of the compound conveniently administered once or twice a day or in sustained release form.

The agents of the invention may be administered in free form or in pharmaceutically acceptable salt form. Such salts may be prepared in conventional manner and exhibit the same order of activity as the free compounds.

Accordingly, the present invention provides an agent of the invention for use as a pharmaceutical, e.g. in the treatment of glaucoma and myopia.

The present invention furthermore provides a pharmaceutical composition comprising an agent of the invention in association with at least one pharmaceutically acceptable diluent or carrier. Such compositions may be formulated in conventional manner. Unit dosage forms contain, for example, from about 0.10 to about 2 mg of an agent according to the invention.

Agents according to the invention may be administered by any conventional route, for example parenterally e.g. in form of injectable solutions or suspensions, or enterally, e.g. in the form of tablets or capsules. Preferably, however, they are applied topically to the eye in ca. 0.01 to 0.5% ophthalmological solutions.

The ophthalmic vehicle is such that the compound is maintained in contact with the ocular surface for a sufficient time period to allow the compound to penetrate the corneal and internal regions of the eye.

The pharmaceutically acceptable ophthalmic vehicle may be e.g. an ointment, vegetable oil, or an encapsulating material.

The preferred agents of the invention for the above-indicated uses are [3R, 4aR, 10aR]-1-methyl-3β-{4-methyl-(4H)-1,2,4-triazo-3-yl}thiomethyl-6-hydroxy-1,2,3,4,4aβ, 5, 10, 10aβ-octahydrobenzo[g]quinoline (compound A), [4a S, 10aR]-1,2,4aβ, 5, 10, 10aβ-hexahydro-6-hydroxy-1-methyl-3-(2-pyridyloxymethyl)-benzo [g]-quinoline (compound B), [4aS, 10 aR]-1,2,4aβ, 5,10,10aβ-hexahydro-6-hydroxy-1-methyl-3-(2-imidazolyl-thiomethyl)-benzo[g] quinoline (compound C) and [3R, 4aR,10 aR]-1-methyl-3β-(2-pyridyl-N-oxide)thiomethyl-6-hydroxy-1,2,3,4,4aα,5,10,10aβ-octahydrobenzo[g]-quinoline (compound D), in free base or acid addition salt form, particularly compound C.

In the above-mentioned intraocular pressure (IOP) test, the compounds A, B, C and D in hydrochloride form reduce IOP in normal rabbits to a maximum of 3.3, 3.8, 3.3 and 4.5 mm Hg respectively, after administration of 0.9 μmol in eye drops, whereas with the same dose of the standard β-blocker Timolol, no decrease of IOP is observed. Additionally, the duration of action of the 4 compounds is unexpectedly long.

In the above-mentioned blood flow test, compound C in hydrochloride form increases blood flow by 30% after administration of 0.1 mg/kg s.c., whereas at doses up to 0.5 mg/kg s.c., Timolol failed to increase blood flow.

The agents of the invention are well tolerated at the dosages administered in the above-indicated tests. Moreover, compounds A, B, C and D show no mutagenicity in *Salmonella typhimurium* (i.e. are negative in the well-known Ames test).

In accordance with the foregoing, the present invention also provides an agent of the invention for use as a pharmaceutical in the treatment of glaucoma and myopia.

Moreover, the present invention provides the use of an agent of the invention, for the manufacture of a medicament for the treatment of glaucoma and myopia.

In still a further aspect, the present invention provides a method for the treatment of glaucoma and myopia in a subject in need of such treatment, which comprises administering to such subject a therapeutically effective amount of an agent of the invention.

The following examples illustrate the invention. The temperatures are given in degrees Celsius and are uncorrected.

EXAMPLE 1

[3R,4aR, 10aR]-1-methyl-3β{-4-methyl-(4H)-1,2,4-triazo-3-yl}thiomethyl-6-hydroxy-1,2,3,4,4aα5,10, 10aβ-octahydrobenzo[g]quinoline a) [3R,4aR,10aR]-1-methyl-3β-hydroxymethyl-6-methoxy-1,2,3,4,4aα,5,10,10aβ-octahydrobenzol[g]quinoline To a solution of 5.78g (20 mM)[3R,4aR,10aR]-1-methyl-3β-methoxycarbonyl-6-methoxy-1,2,3,4,4aα,5,10,10aβ-octahydrobenzo[g]quinoline in 100 ml toluene, a solution of 12 ml SDBA (70% in toluene, 42 mM) is added in drops under argon at room temperature within one hour. Then 10 ml NaOH (30%) are added in drops to the ice cooled reaction mixture. The precipitated crystals are filtered off, washed with water and toluene and dried. The resulting title compound has a m.p. of 148°; $[\alpha]^{20}_D$=-120° (c=0.425 in ethanol).

b)[3R,4aR, 10aR]-1-methyl-3β-mesyloxymethyl-6-methoxy-1,2,3,4,4aα5,10, 10aβ-octahydrobenzo[g]quinoline 12 ml (153 mM) methanesulfochloride are added in drops to a solution of 20 g (76,5 mM) of the compound obtained under a) in 150 ml pyridine at room temperature. The temperature is kept below 45° by ice cooling. After stirring for 2 hours at room temperature, the solution is adjusted to pH 7–8 with saturated $KHCO_3$ solution at 0° and extracted with ethyl acetate. After drying over $Na_2SO_4$, filtering and concentrating by evaporation, the title compound is obtained as beige crystals and directly used for the next step.

c) [3R,4aR, 10aR]-1-methyl-3β{-4-methyl-(4H)-1,2,4-triazo-3-yl}thiomethyl-6-methoxy-1,2,3,4,4aα,5,10,10aβ-octahydrobenzo[g]quinoline A solution of 6 g (17.7 mM) of the compound obtained under b) and 3.1 g (27 mM) 3-mercapto-4-methyl-(4H)-1, 2,4-triazole in 60 ml dimethylformamide is mixed with 6 ml 2N NaOH and stirred at 65° for 18 hours. The so obtained suspension is concentrated by evaporation. The crude product crystallizes. The suspension is cooled to 5–10°, washed with ethyl acetate and dried. Chromatography on silica gel with ethyl acetate containing 10% ethanol and 0.01% $NH_3$ yields the title compound as beige crystals with a m.p. of 205–207°; $[\alpha]^{20}_D$=-107° (c=0.70 in ethanol).

d)[3R,4aR, 10aR]-1-methyl-3β{-4-methyl-(4H)-1,2,4-triazo-3-yl}thiomethyl-6-hydroxy-1, 2,3,4,4aα,5,10, 10aβ-octahydrobenzo[g]quinoline To a solution of 4 g (1 1.2 mM) of the product obtained under c) in 250 ml methylene chloride, 40 ml of boron tribromide (1 M in methylene chloride) are slowly added in drops at a temperature of –40°. The suspension is stirred for 2 hours at room temperature, neutralized with $NH_3$ and extracted with a mixture of 150 ml methylene chloride and 100 ml isopropanol. After drying over $Na_2SO_4$, filtering and concentration by evaporation, the title compound crystallizes. The corresponding hydrochloride crystallizes from methanol/ethanol 1:1 during evaporation. M.p. 185° (decomp.); $[\alpha]^{20}_D$=-77° (c=0.640 in ethanol/water The compounds of formula I as defined in the following table and wherein A and B are each hydrogen are prepared in analogous manner to Example 1:

| Ex. | X | Y | R | M.p. (decomp.) |
|---|---|---|---|---|
| 2 | $CH_2$ | O | 3-(a) ($R_2$=H) | 230° (1) |
| 3 | " | S | 4-(a) ($R_2$=H) | 260° (1) |
| 4 | " | " | (f) ($Z_1$=S, $Z_2$=CH, $R_1$=H) | 280° (1) |
| 5 | " | " | " ($Z_1$=O, $Z_2$=CH, $R_1$=H) | 270° (1) |
| 6 | " | " | 2-(b) | 260° (1) |
| 7 | " | " | (c) ($R_1$=H) | 275° (1) |
| 8 | " | " | (e) ($R_1$=H) | 200° (1) |
| 9 | " | " | (g) | 280° (1) |
| 10 | " | NH | 2-(a) ($R_2$=H) | 275° (1) |
| 11 | " | $NCH_3$ | " | 280° (2) |
| 12 | CO | NH | " | 220° (1) |
| 13 | " | $CH_2$ | " | 215° (1) |
| 14 | " | $OCH_2$ | " | 275° (2) |
| 15 | $CH_2$ | S | (h) | 265° (1) |
| 16 | " | O | 2-(b) | 250° (1) |
| 17 | " | S | (f) ($R_1$=H, $Z_1$=S, $Z_2$=N) | 270° (1) |
| 18 | " | " | (f) ($R_1$=5-$CH_3$, $Z_1$=NH, $Z_2$=CH) | 245° (1) |
| 19 | " | " | (i) ($R_1$=$CH_3$) | 260° |
| 20 | " | " | 2-(a) ($R_2$=o-$CF_3$) | 255° (1) |
| 21 | " | " | 2-(a) ($R_2$=p-$CF_3$) | 250° (1) |
| 22 | " | S=O | 2-(a) ($R_2$=H)* | 240° (1) |
| 23 | " | " | 2-(a) ($R_2$=H)** | 226° (1) |

*(+) - diastereomer
**(−) - diastereomer
(1) Hydrochloride
(2) Dihydrochloride

EXAMPLE 24

[4aS, 10aR]-1,2,4aα,5,10,10aβ-hexahydro-6-hydroxy-1-methyl-3-(2-pyridyloxy-methyl[g] quinoline a) [4aS,10aR]-1,2,4aα,5,10,10aβ-hexahydro-3-hydroxymethyl-6-methoxy-1-methyl-benzo[g]quinoline A solution of 10 g of [4aS,10aR]-3-methoxycarbonyl-1, 2,4aα,5,10,10aβ-hexahydro-6-methoxy-1-methyl-benzo[g] quinoline in 50 ml tetrahydrofuran is added in drops at 5° to a suspension of 2.9 g lithium aluminum hydride in 200 ml of tetrahydrofuran and the reaction mixture is stirred at room temperature overnight. The excess of lithium aluminum hydride is hydrolized by addition in drops of a water/tetrahydrofuran solution, the precipitate is filtered off, the filtrate is concentrated and the residue is triturated with ether. The title compound is obtained as crystals melting at 142–143°; $[\alpha]^{20}_D$=-222.8° (c=3.5 in dimethylformamide).

b) [4aS, 10aR]-1 2,4aα,5,10,10aβ-hexahydro-6-methoxy-1-methyl-3-(2-pyridyloxymethyl)-benzo[g]quinoline 4.62 g sodium hydride (60% oil emulsion) are added in portions to a solution of 15 g of the compound obtained under a) in 500 ml dimethylformamide. The suspension is heated at 60° till termination of the hydrogen evolution, before addition of 12 ml of 2-chloropyridine. The reaction mixture is stirred for 6 hours at 60°, quenched with $NH_4Cl$, concentrated by evaporation and extracted with water/methylene chloride, followed by flash chromatography of the organic phase on silica gel with methyl-t.butylether/MeOH (96/4). The crude title compound is transformed into its hydrochloride which crystallizes from EtOH/$Et_2O$. M.p.= 244–247°; $[\alpha]^{20}_D$=-98.4° (c=0.62 in dimethylformamide).

c) [4aS,10aR]-1,2,4aα,5,10,10aβ-hexahydro-6-hydroxy-1-methyl-3-(2-pyridyloxymethyl)-benzo[g]quinoline The methylether cleavage is effected with boron tribromide analogously to Example 1d), starting from the compound obtained under b) above. The corresponding hydrochloride has a m.p. of 223–225°; $[\alpha]^{20}_D$=-125.6° (c=0.45 in dimethylformamide).

The compounds of formula I as defined in the following table and wherein A and B from together an additional bond are prepared in analogous manner to Example 1:

| Ex. | X | Y | R | M.p |
|---|---|---|---|---|
| 25 | CH₂ | O | 2-(a) (R₂=H) | 223–225° (1) |
| 26 | " | S | (e) (R₁=H) | 226–228°* (1) |
| 27 | " | " | 4-(a) (R₂=H) | 200–202° (2) |
| 28 | " | " | (c) (R₁=H) | 230°* (1) |
| 29 | " | " | (d) (R₁=CH₃) | 230–232° (2) |
| 30 | " | O | 4-(a) (R₂=H) | 235°* (2) |

*(decomp.)
(1) hydrochloride
(2) dihydrochloride

What is claimed is:

1. A compound of formula I

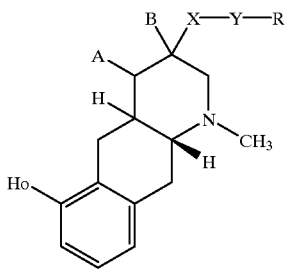

I wherein,

A and B are each H or form together an additional bond,

X is CH₂ or CO,

Y is O, S, S=O, NR₁, CH₂, or O—CH₂, wherein R₁ is H or $C_{1-4}$ alkyl, and

R is selected from the group consisting of formulae (b), (c), (d), (e), (f), (g), (h) and (i)

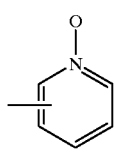

(b)

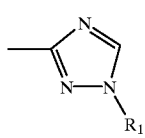

(c)

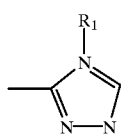

(d)

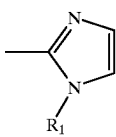

(e)

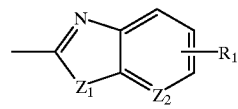

(f)

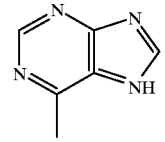

(g)

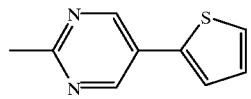

(h)

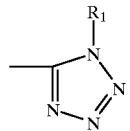

(i)

wherein R₁ is defined above, R₂ is H or trifluoromethyl, Z₁ is O, S or NH and Z₂ is CH or N, provided that if X is CH₂, Y is S and R is of formula (a) wherein the free bond is adjacent to the nitrogen and R₂ is H, then A and B are not H, in free base or acid salt form.

2. A compound of formula I as defined in claim 1, wherein A and B and X are as defined in claim 1, Y is O, S, NR₁ (CH₂ or O—CH₂, wherein R₁ is H or (CH$_{1-4}$)alkyl, and R is selected from the group consisting of formula (a), (b), (c), (d) and (g), wherein R₁ is as defined above and R₂ is H, of formula (e) or (f), wherein R₁ is H, Z₁ is O or S and Z₂ is CH, in free base or acid addition salt form.

3. A compound of claim 1 selected from [3R, 4aR, 10aR]-1-methyl-3β-{4-methyl-(4H)- 1,2,4-triazo-3-yl}thiomethyl-6-hydroxy- 1,2,3,4,4aα, 5,10,10aβ-octahydrobenzo [g]quinoline, [4aS, 10aR]-(,1,2,4aα), 5,10, 10aβ-hexahydro-6-hydroxy-1-methyl-3-(2-pyridyloxymethyl)-benzo[g]quinoline, [4aS, 10aR]-1,2,4aα, 5,10,10aβ-hexahydro-6-hydroxy-1-methyl-3-(2-imidazolyl-thiomethyl)-benzo[g]quinoline and[3R, 4aR, 10aR]-1-methyl-3β-(2-pyridyl-N-oxide)thiomethyl-6-hydroxy-1,2,3,4,4aα, 5,10,10aβ-octahydrobenzo[g]-quinoline, in free base or acid addition salt form.

4. A process for the preparation of a compound of formula I as defined in claim 1, or a salt thereof, which includes the step of converting, in a compound of formula II

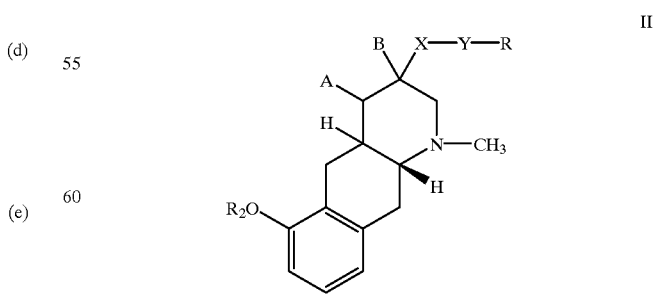

II wherein A, B, X, Y and R are as defined in claim 1 and R₂ is (C$_{1-4}$)alkyl, the alkoxy group into a hydroxy group and recovering the thus obtained compound of formula I in free base or acid addition salt form.

5. A pharmaceutical composition comprising the compound of claim 1.

6. A pharmaceutical composition for use in treatment of glaucoma and myopia, comprising the compound of claim 1 in free base or pharmaceutically acceptable acid addition salt form.

7. A pharmaceutical composition comprising a compound of claim 1 in free base or pharmaceutically acceptable acid addition salt form, in association with a pharmaceutical carrier or diluent.

8. A method for the treatment of glaucoma and myopia in a subject in need of such treatment, which comprises administering to such subject a therapeutically effective amount of a compound of claim 1 in free base or pharmaceutically acceptable acid addition salt form.

9. A method for treating an eye aliment, comprising the step of administering a therapeutically effective amount of a compound

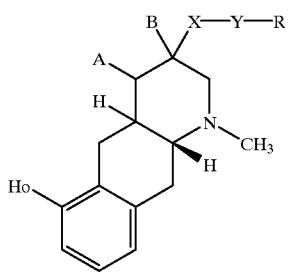

I wherein

A and B are each H or form together an additional bond,

X is $CH_2$ or CO,

Y is O, S, S=O, $NR_1$, $CH_2$, or O—$CH_2$, wherein $R_1$ is H or $C_{1-4}$ alkyl, and R is selected from the& group consisting of formulae (a), (b), (c), (d), (e), (F), (g), (h) and (i)

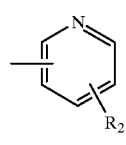
(a)

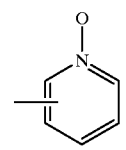
(b)

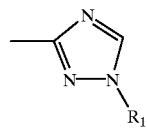
(c)

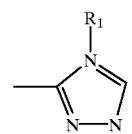
(d)

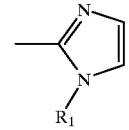
(e)

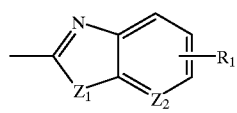
(f)

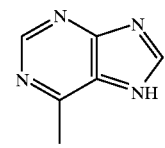
(g)

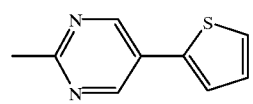
(h)

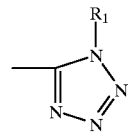
(i)

wherein $R_1$ is defined above, $R_2$ is H or trifluoromethyl, $Z_1$ is O, S or NH and $Z_2$ is CH or N, provided that if X is $CH_2$, Y is S and R is of formula (a) wherein the free bond is adjacent to the nitrogen and $R_2$ is H, then A and B are not H, in free base or acid salt form.

10. The method of claim 9 wherein said compound is in free base or pharmaceutically acceptable acid addition salt form.

11. The method of claim 9 wherein R is formula (a), (b), (c), (d) or (g) wherein $R_2$ is H, or R is formula (e) or (f) wherein $R_1$ is H, $Z_1$, is O or S and $Z_2$ is CH, in free base or acid addition salt form.

12. The method of claim 9 wherein said ailment is glaucoma or atrophy of the optic nerve.

* * * * *